US007842285B2

(12) United States Patent
Lu et al.

(10) Patent No.: US 7,842,285 B2
(45) Date of Patent: Nov. 30, 2010

(54) COSMETIC COMPOSITIONS AND METHODS OF USE

(75) Inventors: Shaoxiang Lu, Plainsboro, NJ (US); Wei Hong Yu, Edison, NJ (US); Hy Si Bui, Piscataway, NJ (US)

(73) Assignee: L'Oreal, Paris (FR)

( * ) Notice: Subject to any disclaimer, the term of this patent is extended or adjusted under 35 U.S.C. 154(b) by 1408 days.

(21) Appl. No.: 11/266,301

(22) Filed: Nov. 4, 2005

(65) Prior Publication Data

US 2006/0110347 A1 May 25, 2006

Related U.S. Application Data

(60) Provisional application No. 60/624,539, filed on Nov. 4, 2004.

(51) Int. Cl.
*A61Q 1/04* (2006.01)
*A61Q 1/06* (2006.01)

(52) U.S. Cl. .................. 424/64; 424/70.12; 424/401

(58) Field of Classification Search ........................ None
See application file for complete search history.

(56) References Cited

U.S. PATENT DOCUMENTS

| | | | |
|---|---|---|---|
| 4,289,891 A | 9/1981 | Brown et al. | |
| 5,480,637 A | 1/1996 | Smith | |
| 5,851,277 A | 12/1998 | Muller-Rees et al. | |
| 5,961,998 A | 10/1999 | Arnaud et al. | |
| 6,051,216 A | 4/2000 | Barr et al. | |
| 6,325,996 B1 | 12/2001 | Shinojima et al. | |
| 6,905,696 B2 * | 6/2005 | Marotta et al. | ............... 424/401 |
| 2002/0004054 A1 | 1/2002 | Calello et al. | |
| 2002/0159960 A1 | 10/2002 | Scancarella et al. | |
| 2004/0151680 A1 * | 8/2004 | Patil et al. | ................. 424/70.12 |

FOREIGN PATENT DOCUMENTS

| | | |
|---|---|---|
| JP | 07-089844 | 4/1995 |
| JP | 8-127719 | 5/1996 |
| JP | 11-255616 | 9/1999 |
| JP | 2000-281534 | 10/2000 |
| JP | 2000-281535 | 10/2000 |
| JP | 2001-039817 | 2/2001 |
| JP | 2001-114648 | 4/2001 |
| JP | 2001-294515 | 10/2001 |
| JP | 2002-154916 | 5/2002 |
| JP | 2002-255827 | 9/2002 |
| JP | 3436745 | 8/2003 |
| JP | 2004-315420 | 11/2004 |

OTHER PUBLICATIONS

Patent Abstracts of Japan, JP 07-330630, Dec. 19, 1995.
Patent Abstracts of Japan, JP 07-330549, Dec. 19, 1995.
Office Action as received in corresponding Japanese Application No. 2005-320506 dated May 22, 2007 (w/English Translation).

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

The present invention relates to a cosmetic composition containing a phenyl substituted organosiloxane to provide shine and/or gloss when applied to a keratinous material, such as skin.

17 Claims, No Drawings

COSMETIC COMPOSITIONS AND METHODS OF USE

BACKGROUND OF THE INVENTION

1. Field of the Invention

The present invention relates to a cosmetic composition containing a phenyl substituted organosiloxane to provide shine and/or gloss when applied to a keratinous material, such as skin.

2. Description of the Background

Many cosmetic compositions, including pigmented cosmetics such as foundations, concealers, lipsticks, mascaras, and other cosmetic and sunscreen compositions have been developed for longer wear and transfer resistance properties. This is accomplished by the use of compositions that form a film after application. Such compositions generally contain volatile solvents, which evaporate on contact with the skin or other keratinous tissue, leaving behind a layer comprising waxes and/or resins, pigments, fillers, and actives. However, these compositions tend to be uncomfortable for the wearer as the composition remains on the skin or other keratinous tissue as a brittle or non-flexible film. Furthermore, such compositions tend to have a matte finish whereas consumers tend to favor compositions that appear shiny and/or glossy.

There remains a need to provide cosmetic compositions which are long-wearing, transfer-resistant and comfortable to wear with improved appearance such as shine and gloss.

Accordingly, one aspect of the present invention is a care and/or makeup and/or treatment composition for keratinous material such as the skin and/or the lips, which is able to address or overcome at least one of the aforementioned problems with the prior art compositions.

SUMMARY OF THE INVENTION

The invention provides a layered lip composition, wherein at least one composition of the layered lip composition comprises at least one phenyl substituted organosiloxane.

The invention also provides a composition suitable for topical administration to a keratinous surface which comprises at least one phenyl substituted organosiloxane which is essentially free of volatile compounds, such as volatile solvents.

The invention also provides a composition suitable for topical administration to a keratinous surface which comprises at least one phenyl substituted organosiloxane and which may further include an emollient and/or a wax.

The invention also provides a cosmetic composition suitable for topical administration to a keratinous surface which comprises at least about 50% by weight of the composition of at least one phenyl substituted organosiloxane and preferably also contains an ester.

The invention also provides a layered lip composition, wherein a first layer comprises at least phenyl substituted organosiloxane and a second layer comprises at least one polyorganosiloxane.

The invention also provides a cosmetic composition suitable for topical administration to a keratinous surface which comprises at least one phenyl substituted organosiloxane and at least one film forming sucrose acetate isobutyrate.

The invention also provides kits of the above compositions.

The invention also provides a method of making-up and/or treating at least one keratinous surface on a user by applying one or more of the compositions, layered compositions and/or employing kits comprising the compositions.

DETAILED DESCRIPTION OF THE INVENTION

All percentages are percentages by weight unless otherwise indicated.

As used herein, the expression "at least one" means one or more and thus includes individual components as well as mixtures/combinations.

The cosmetic compositions and methods of the present invention can comprise, consist of, or consist essentially of the essential elements and limitations of the invention described herein, as well as any additional or optional ingredients, components, or limitations described herein or otherwise useful in personal care compositions intended for topical application to the skin.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

"Film former" or "film forming agent" as used herein means a polymer that, after dissolution in at least one solvent (such as, for example, water and organic solvents), leaves a film on the substrate to which it is applied, for example, once the at least one solvent evaporates, absorbs and/or dissipates on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human lips followed by "kissing" a material, for example, a sheet of paper, after expiration of a certain amount of time following application, such as 2 minutes after application. Similarly, transfer resistance of a composition may be evaluated by the amount of product transferred from a wearer to any other substrate, such as transfer from the neck of an individual to a collar after the expiration of a certain amount of time following application. The amount of composition transferred to the substrate (e.g., collar, or paper) may then be evaluated and compared. For example, a composition may be transfer resistant if a majority of the product is left on the wearer, e.g., lips, neck, etc. Further, the amount transferred may be compared with that transferred by other compositions, such as commercially available compositions. In a preferred embodiment of the present invention, little or no composition is transferred to the substrate.

"Long wear" as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to human skin (including lips) and evaluating the consistency, texture and color of the composition after an extended period of time. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Tackiness" as used herein refers to measuring the maximum tensile force, $F_{max}$, required while separating two surfaces. Depending on the application envisaged and the formulation being designed, the desirable value for $F_{max}$ may vary. In some embodiments, the substantially non-tacky compositions have a $F_{max}$ of less than about 4 Newton (N), less than about 1 N, less than about 0.5 N, less than about 0.3 N, less than about 0.2 N or less than 0.1 N. One of ordinary skill in the art can determine the $F_{max}$ of the composition by, for example, determining the maximum force of traction, measured with an extensiometer of the LLOYD model LR5K type, needed to detach two surfaces.

For example, two 38 mm$^2$ surfaces, A and B, which are solid, rigid, inert, and non-absorbing, are mounted on movable mounts, facing each other. The surfaces may be movable either toward or away from each other, or one may move surface A independently from surface B or vice versa. Prior to insertion into the extensiometer, surface A is coated with the composition to be measured, which may be dissolved in a solvent such as aqueous, hydroalcoholic, hydrocarbon, silicone, and alcoholic solvents in a concentration of from about 10 to about 30%, preferably 20%, the surface A is coated in a thickness of from 1 to 10 mil, preferably 1 mil, and the surface is dried for 24 hours at room temperature, e.g., 22 to 25° C., at a relative humidity of about 50%. Once inserted in the extensiometer, surface A is subjected for 20 seconds to a compression force of 3 N against surface B and then subjected for 30 seconds to tensile force at a rate of 20 mm/minute. The amount of force, $F_{max}$, needed to obtain initial separation is then noted. A mean $F_{max}$ is determined by carrying out the procedure with multiple pairs, preferably at least six pairs, of surface A and surface B.

In compositions comprising at least one phenyl substituted organosiloxane, the compositions preferably have a refractive index of greater than about 1.5.

The phenyl substituted organosiloxane may be present in an amount suitable for providing gloss to the keratinous material and can be present in an amount from about 0.1 to about 95% by weight of the composition, including 0.5, 1, 1.5, 5, 10, 15, 20, 25, 30, 35, 40, 45, 50, 55, 60, 65, 70, 75, 80, 85, and 90% by weight of the composition, inclusive of all values and ranges there between. In one embodiment, the phenyl substituted organosiloxane is present in an amount of at least 50% by weight of the composition.

The phenyl substituted organosiloxanes, in one embodiment, are defined by the following formula:

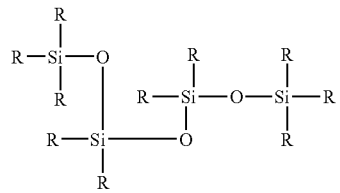

wherein R is a methyl or phenyl and wherein there are at least three phenyl groups in the organosiloxane. In certain embodiments, there are least four phenyl groups or five phenyl groups.

In another embodiment, the phenyl substituted organosiloxanes are defined by the following formula:

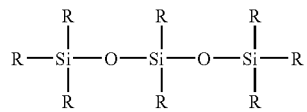

wherein R is a methyl or phenyl and where there are at least three phenyl groups in the organosiloxane. In certain embodiments, there are least four phenyl groups or five phenyl groups.

Mixtures of the above described phenyl substituted organosiloxanes may also be used. Suitable phenyl substituted organosiloxanes, for example, include mixtures having triphenyl substituted mixed with tetra and pentyl phenyl substituted organosiloxane. The phenyl substituted organosiloxanes may be purchased from a variety of commercial sources. Suitable sources include Dow Corning, for example, one preferred source is Dow Corning 555 Cosmetic Fluid having the INCI name trimethyl pentaphenyl trisiloxane, which is a mixture of about 60 to 90 parts trimethylpentaphenyltrisiloxane and from about 10 to 30 parts hexaphenyltetrasiloxane. In addition, Dow Corning 554 Cosmetic Fluid may also be used.

Further, the composition comprising phenyl substituted organosiloxane(s) may also include at least one polyester of glycerol oligomers, for example, polyglyceryl-2, polyglyceryl-3 and bis-diglycerylpolyacyladipate-2.

Further, the composition comprising phenyl substituted organosiloxane(s) may also include at least one wax. Examples of waxes that can be included are waxes chosen from known animal, fossil, vegetable, mineral or synthetic waxes, such as paraffin waxes, polyethylene waxes, carnauba or candelilla waxes, beeswaxes, lanolin wax, chinese insect waxes, rice wax, ouricury wax, esparto wax, cork fibre wax, sugarcane wax, japan wax, sumach wax, montan wax, microcrystalline waxes, ozokerite, the waxes obtained by the Fischer-Tropsch synthesis, silicone waxes or their mixtures.

Further, the composition comprising phenyl substituted organosiloxane(s) may also include at least one C1-C30 mono- and poly-esters of sugars and related compounds, for example such as sucrose polyesters.

In one embodiment, the composition comprising phenyl substituted organosiloxane(s) may also include a film forming sucrose acetate isobutyrate, preferably one which is of food and/or cosmetic grade. The sucrose acetate isobutyrate can be included in such compositions in an amount of from 1 to 50% by weight of the composition, including 5, 10, 15, 20, 25, 30, 35, 40, 45% and all values and subranges there between, for example, from 1 to 30% by weight of the composition.

In one embodiment, the composition comprising phenyl substituted organosiloxane(s) can be solid. In another embodiment, the composition can be semi-solid. In another embodiment, the composition can be liquid. The composition comprising phenyl substituted organosiloxane can also contain additional additives conventionally used in cosmetics, examples of which are described below. In one embodiment, the composition comprising phenyl substituted organosiloxane comprises at least one of an emollient and/or a wax.

In one embodiment, the composition comprising phenyl substituted organosiloxane comprises at least one of a wax and/or oil. In this embodiment, the phenyl substituted organosiloxane may not be compatible with the oil present and thus a wax can be used to compatibilize the oil and organosiloxane. In another embodiment, the phenyl substituted organosiloxane may not be compatible with the wax and then an oil would be included that compatibilizes the wax and organosiloxane.

In one embodiment, the composition comprising phenyl substituted organosiloxane is essentially free of volatile compounds, such as volatile solvents. "Substantially free of volatile compounds" as used herein means that the composition contains less than about 0.5% volatile compounds, and "devoid of volatile compounds" as used herein means that the composition contains less than about 0.1% volatile compounds. In a preferred embodiment, the compositions of the present invention are "free of volatile compounds," meaning no detectable quantities of volatile compounds are in the composition, it being understood to one of skill in the art that some undetectable quantity of volatile compounds may be present.

The compositions comprising phenyl substituted organosiloxane(s) may be employed in a layered make-up composition, e.g., comprising two layers, such that the compositions comprising phenyl substituted organosiloxane(s) comprise components for providing shine and gloss when applied over at least one base coat and is defined herein as "a top coat" or "a second composition." In certain embodiments, the top coat is not compatible with the base coat thereby avoiding, in part or in whole, the dissolution, disruption and/or smearing of the base coat when the top coat is applied.

The compositions comprising phenyl substituted organosiloxanes may be in the form of a structured molded composition, such as a stick. Such a structured molded composition can be used to apply make-up to the skin, hair, lips or other keratinous material and typically include a liquid fatty phase structured with one or more structuring agents. The phenyl substituted organosiloxane or mixtures of these increase the shine and/or gloss of otherwise dull and/or matte appearance when the a structured molded composition is applied to a keratinous surface.

When the compositions comprising phenyl substituted organosiloxane(s) are employed in a layered composition, a base coat is employed. The base coat (also referred to as a "first composition") is a transfer resistant cosmetic composition, which may also be pliable and/or comfortable to wear upon application to a keratinous surface, comprising at least one polyorganosiloxane containing polymer comprising at least one moiety comprising: at least one polyorganosiloxane group comprising organosiloxane units in the chain of the moiety or in the form of a graft, and at least two groups capable of establishing hydrogen interactions, e.g., hydrogen bonding. The base coat composition can be formulated in a liquid fatty phase.

In accordance with certain aspects of the present invention, the phrase "liquid fatty phase" is understood to mean a fatty phase, which is liquid at room temperature (25° C.) and atmospheric pressure (760 mmHg), and which comprises one or more fatty substances that are liquid at room temperature, also known as oils, which are compatible with one another.

In accordance with certain aspects of the present invention, the phrase "structured liquid fatty phase" is understood to mean that this structured phase does not run between the fingers and is at least thickened.

Where the liquid fatty phase is structured, it makes it possible to limit exudation of the fatty phase from solid compositions, and furthermore, to limit, after deposition on the skin or the lips, its migration into the wrinkles and fine lines, which is desired for compositions such as a lipstick or an eyeshadow. Significant migration of the liquid fatty phase, laden with coloring materials, leads to an unaesthetic effect around the lips or the eyes, which can accentuate the wrinkles and fine lines. This migration is often mentioned by women as being a major defect of conventional lipsticks and eyeshadows. The term "migration" is understood to mean running of the composition deposited on the lips or skin beyond its initial outline.

The base coat composition of the present invention may be in any form. For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. The base coat composition can also be in a form chosen from a translucent anhydrous gel and a transparent anhydrous gel. The base coat composition of the invention may, for example, comprise an external or continuous fatty phase. The base coat composition may be anhydrous. In another embodiment, the base coat composition of the invention may be transparent or clear, including for example, a base coat composition without pigments. The base coat composition can also be a molded composition or cast as a stick or a dish. The base coat composition in one embodiment is a solid such as a molded stick or a poured stick. The base coat compositions of the present invention may also be in the form a lip composition such as a lipstick or a liquid lip color, a foundation or a mascara, which exhibit excellent and improved properties of transfer-resistance, flexibility, pliability, adherence and lack of tackiness.

Where the base coat composition of the invention is not-liquid, the structuring of the liquid fatty phase can be controlled by the type of structuring polymer used and is such that a rigid structure in the form of a stick, of good mechanical resistance, can be obtained. These rigid compositions, when colored, allow for a supple, light, non-transfer, non-migrating and/or long-wearing applications on a keratinous surface. Such compositions may contain one or more structuring polymers.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8 week test at 40° C., 37° C., 45° C., 50° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

Polyorganosiloxane Containing Polymer

According to the present invention, base coat compositions comprise at least one polyorganosiloxane containing polymer chosen from homopolymers and copolymers, preferably, with a weight-average molecular mass ranging from about 500 to about $2.5 \times 10^6$ or more, comprising at least one moiety comprising: at least one polyorganosiloxane group comprising, preferably, from 1 to about 35,000 organosiloxane units in the chain of the moiety or in the form of a graft, and at least two groups capable of establishing hydrogen interactions.

According to preferred embodiments of the present invention, the polyorganosiloxane-containing polymers may belong to the following two families:

a) polyorganosiloxanes comprising at least two groups capable of establishing hydrogen interactions, these two groups being located in the polymer chain; and/or b) polyorganosiloxanes comprising at least two groups capable of establishing hydrogen interactions, these two groups being located on grafts or branches.

The polyorganosiloxane containing polymers can be liquid or solid at room temperature. Preferably, the polymers are solid. When the polymers are solid, it is preferable that they can be dissolved before or during use in a solvent, for instance isododecane. These solvents may then be stored in the composition or may be removed by selective evaporation, which is well known to those skilled in the art.

The polymers comprising two groups capable of establishing hydrogen interactions in the polymer chain may be polymers comprising at least one moiety corresponding to the formula:

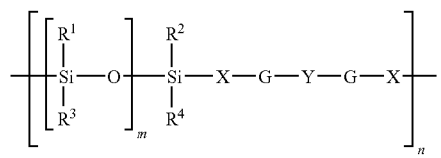
(I)

in which:

1) $R^1$, $R^2$, $R^3$ and $R^4$, which may be identical or different, represent a group chosen from:

linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^5$ represents a linear or branched $C_1$ to $C_{50}$ alkyl group or a polyorganosiloxane chain, possibly comprising one or more ester, amide, urethane, thiocarbamate, urea, thiourea and/or sulphonamide groups, which may be linked to another chain of the polymer;

5) the groups G, which may be identical or different, represent divalent groups chosen from:

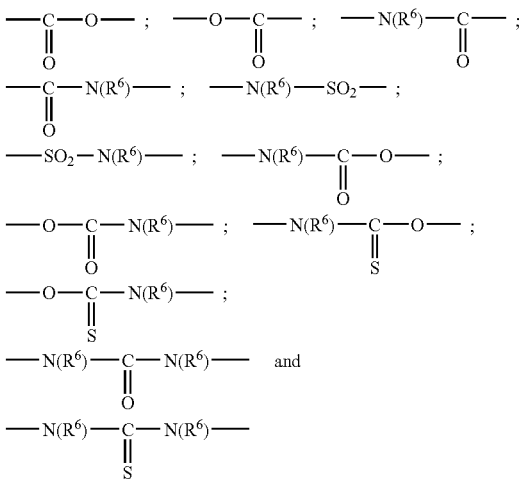

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

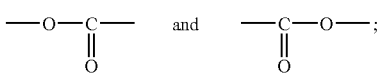

6) n is an integer of at least 1, including at least 100, 500, 600, 700, 900, 1000, for example ranging from 2 to 500 and preferably from 2 to 200, including all values and subranges there between; and m is an integer of at least one, ranging from 1 to 35,000, including at least 100, 500, 600, 700, 900, 1000, 2000, 5000, 10,000, 15,000, 20,000, 25,000 and all values and subranges there between, for example, from 1 to 10,000 and 1 to 2,500, from 1 to 700 and from 6 to 200.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) $C_{30}$ to $C_{56}$ branched alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

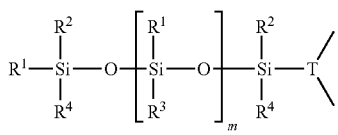

in which $R^1$, $R^2$, $R^3$, $R^4$, T and m are as defined above, and h) polyorganosiloxane chains of formula:

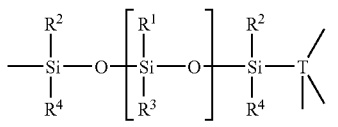

The polyorganosiloxanes of the second family may be polymers comprising at least one moiety corresponding to formula (II):

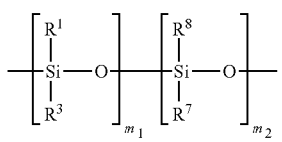

(II)

in which $R^1$ and $R^3$, which may be identical or different, are as defined above for formula (I), $R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above, $m_1$ is an integer of at least one ranging from 1 to 35,000, including at least 100, 500, 600, 700, 900, 1000, 2000, 5000, 10,000, 15,000, 20,000, 25,000 and all values and subranges there between, for example, from 1 to 10,000 and 1 to 2,500, from 1 to 700, and from 6 to 200, including all values and subranges there between; and $m_2$ is an integer of at least one ranging from 1 to 35,000, including at least 100, 500, 600, 700, 900, 1000, 2000, 5000, 10,000, 15,000, 20,000, 25,000 and all values and subranges there between, for example, from 1 to 10,000 and 1 to 2,500, from 1 to 700, and from 6 to 200, including all values and subranges there between.

The polyorganosiloxane containing polymer may be a homopolymer, that is to say a polymer comprising several identical moieties, in particular moieties of formula (I) or of formula (II).

It is also possible to use a polymer consisting of a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to preferred embodiments, it is also possible to use a copolymer comprising at least one hydrocarbon-based moiety comprising two groups capable of establishing hydrogen interactions, chosen from ester, amide, sulphonamide, carbamate, thiocarbamate, urea and thiourea groups, and combinations thereof.

These copolymers may be block copolymers or grafted copolymers.

According to a first embodiment of the invention, the groups capable of establishing hydrogen interactions are amide groups of formulae —C(O)NH— and —HN—C(O)—.

In this case, the polymer may comprise at least one moiety of formula (III) or (IV):

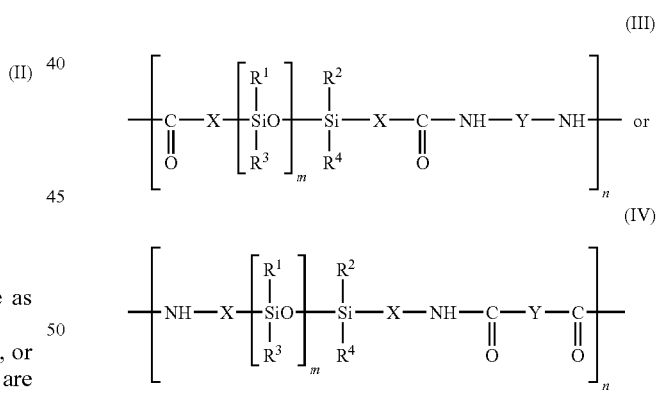

in which $R^1$, $R^2$, $R^3$, $R^4$, X, Y, m and n are as defined above.

Such a moiety may be obtained:

either by a condensation reaction between a silicone containing α, ω-carboxylic acid ends and one or more diamines, according to the following reaction scheme:

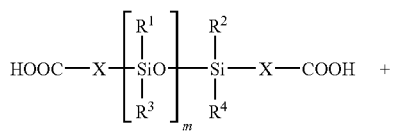

-continued $$H_2N-Y-NH_2 \longrightarrow$$

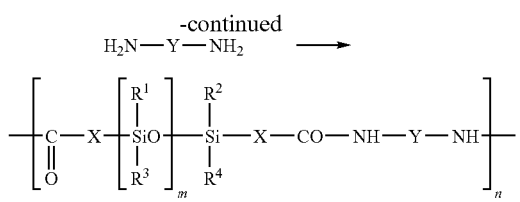

or by reaction of two molecules of α-unsaturated carboxylic acid with a diamine according to the following reaction scheme:

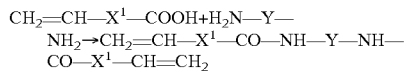

followed by the addition of a siloxane to the ethylenic unsaturations, according to the following scheme:

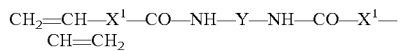

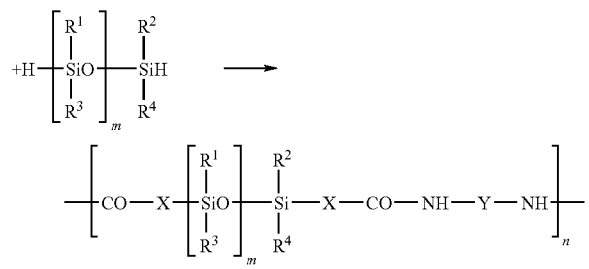

in which $X^1$—$(CH_2)_2$— corresponds to X defined above and Y, $R^1$, $R^2$, $R^3$, $R^4$ and m are as defined above;

or by reaction of a silicone containing α,ω-$NH_2$ ends and a diacid of formula HOOC—Y—COOH according to the following reaction scheme:

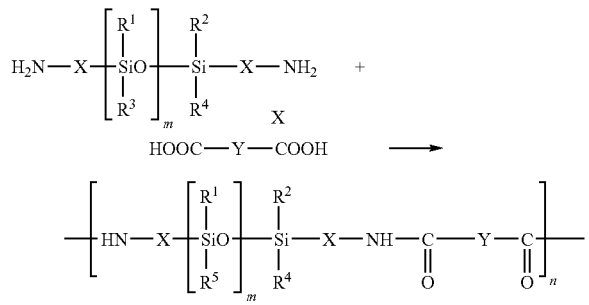

In these polyamides of formula (III) or (IV), m is an integer of at least one as defined above, and preferably in the range from 1 to 700, for example, from 15 to 500 and from 15 to 45, including all values and subranges there between; and n is in particular in the range from 1 to 500, for example, from 1 to 100 and from 4 to 25, including all values and subranges there between; X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, including from 1 to 20 carbon atoms and from 2 to 6 carbon atoms, including all values and subranges there between, for example, 6 carbon atoms.

In formulae (III) and (IV), the alkylene group representing X or Y can optionally contain in its alkylene portion at least one of the following elements:

1) 1 to 5 amide, urea or carbamate groups,
2) a $C_5$ or $C_6$ cycloalkyl group, and
3) a phenylene group optionally substituted with 1 to 3 identical or different $C_1$ to $C_3$ alkyl groups.

In formulae (III) and (IV), the alkylene groups may also be substituted with at least one element chosen from the group consisting of:

a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which $R^5$ represents a polyorganosiloxane chain and T represents a group of formula:

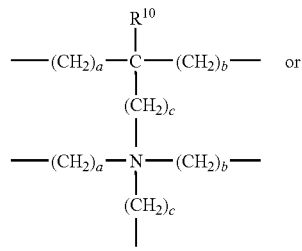

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

(V)

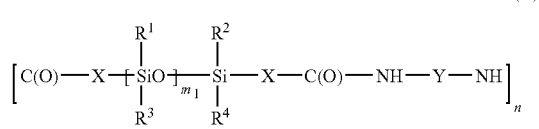

-continued

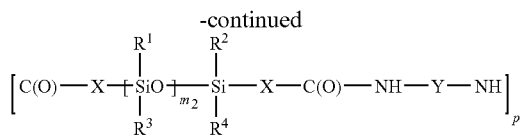

in which X, Y, n and $R^1$ to $R^4$ have the meanings given above, $m_1$ and $m_2$, which are different, are as defined above, and preferably are chosen in the range from 1 to 1 000, and p is at least one for example ranging from 2 to 500 and preferably from 2 to 200.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

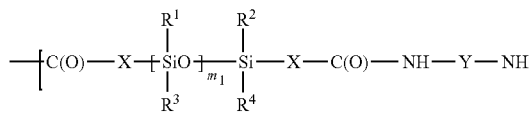

(VI)

in which $R^1$ to $R^4$, X, Y, $m_1$, $m_2$, n and p have the meanings given above and $Y^1$ is different from Y but chosen from the groups defined for Y. As previously discussed, the various moieties may be structured to form either a block copolymer, or a random copolymer or an alternating copolymer.

In one embodiment, the polyorganosiloxane-containing polymer may also contain a grafted copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

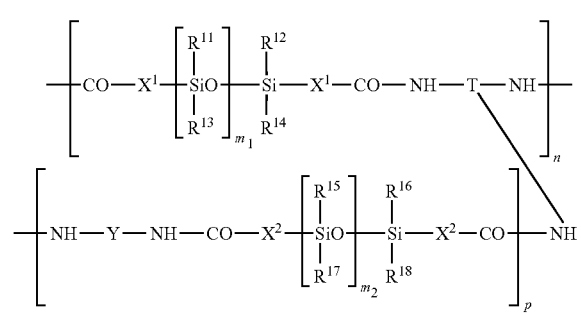

(VII)

in which $X^1$ and $X^2$, which may be identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1,000, and p is an integer of at least one, for example, p can range from 2 to 500.

In formula (VII), it is preferred that:

p is in the range from 1 to 25, including from 1 to 7, including all values and subranges there between, $R^{11}$ to $R^{18}$ are methyl groups, T corresponds to one of the following formulae:

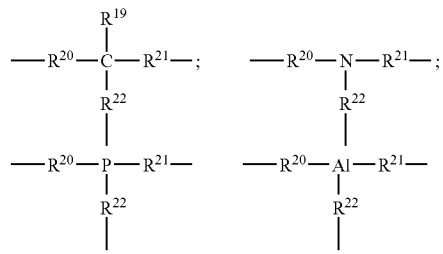

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

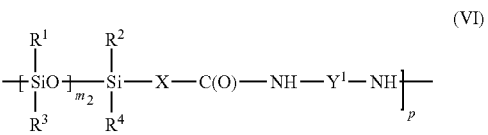

in particular with $R^{20}$, $R^{21}$ and $R^{22}$ representing —$CH_2$—$CH_2$—, $m_1$ and $m_2$ are in the range from 15 to 500, including from 15 to 45 and including all values and subranges there between, $X^1$ and $X^2$ represent —$(CH_2)_{10}$—, and Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

The siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

The preferred siloxane-based polyamides are:

polyamides of formula (III) in which m is from 15 to 300, for example, 15 to 100, including all values and subranges there between;

mixtures of two or more polyamides in which at least one polyamide has a value of m in the range from 15 to 50, including all values and subranges there between and at least one polyamide has a value of m in the range from 30 to 300, including all values and subranges there between;

polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the corresponding portion $m_2$ representing 1% to 99% by weight of the total weight of the polyamide;

mixtures of polyamide of formula (III) combining 1) 80% to 99% by weight of a polyamide in which n is equal to 2 to 10 and in particular 3 to 6, and 2) 1% to 20% of a polyamide in which n is in the range from 5 to 500 and in particular from 6 to 100;

polyamides corresponding to formula (VI) in which at least one of the groups Y and $Y^1$ contains at least one hydroxyl substituent;

polyamides of formula (III) synthesized with at least one portion of an activated diacid (diacid chloride, dianhydride or diester) instead of the diacid;

polyamides of formula (III) in which X represents —(CH$_2$)$_3$— or —(CH$_2$)$_{10}$—; and polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:

a $C_1$ to $C_{50}$ alkyl ester group by introducing a $C_1$ to $C_{50}$ monoalcohol during the synthesis, a $C_1$ to $C_{50}$ alkylamide group by taking as stopping group a monoacid if the silicone is α,ω-diaminated, or a monoamine if the silicone is an α,ω-dicarboxylic acid.

According to one embodiment of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based polymers containing silicones may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and for example, 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare polyamide based polymer containing silicones on a copolymer between a hydrocarbon-based polyamide and a silicone polyamide, by transamidation of a polyamide having, for example, an ethylene-diamine constituent, with an oligosiloxane-α,ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:

by hydrosilylation of unsaturated bonds in polyamides based on fatty acid dimers;

by silylation of the amide groups of a polyamide; or by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

The polyorganosiloxane containing polymers used in the composition of the invention are most preferably polymers of the polyorganosiloxane type such as those described in documents U.S. Pat. No. 5,874,069, U.S. Pat. No. 5,919,441, U.S. Pat. No. 6,051,216 and U.S. Pat. No. 5,981,680, the entire disclosures of which are hereby incorporated by reference.

According to another embodiment of the invention, the polyorganoxilixane containing polymer is a homopolymer or a copolymer comprising urethane or urea groups.

As previously discussed, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

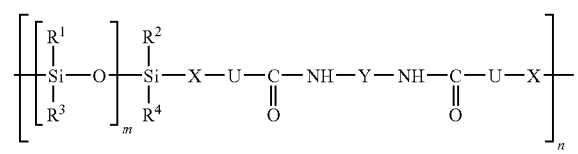

(VIII)

in which $R^1$, $R^2$, $R^3$, $R^4$, X, Y, m and n have the meanings given above for formula (I), and U represents —O— or —NH—, such that:

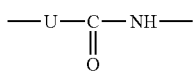

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

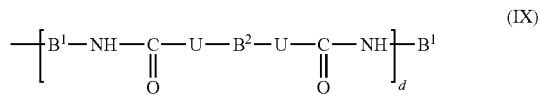

(IX)

in which $B^1$ is a group chosen from the groups given above for Y, U is —O— or —NH— and $B^2$ is chosen from:

linear or branched $C_1$ to $C_{40}$ alkylene groups, which can optionally bear an ionizable group such as a carboxylic acid or sulphonic acid group, or a neutralizable or quaternizable tertiary amine group, $C_5$ to $C_{12}$ cycloalkylene groups, optionally bearing alkyl substituents, for example one to three methyl or ethyl groups, or alkylene, for example the diol radical: cyclohexanedimethanol, phenylene groups that may optionally bear $C_1$ to $C_3$ alkyl substituents, and groups of formula:

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

T can represent, for example:

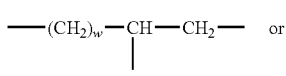 or

-continued

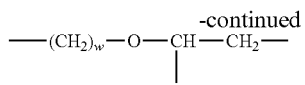

with w being an integer ranging from 1 to 10 and $R^5$ being a polyorganosiloxane chain.

When Y is a linear or branched $C_1$ to $C_{40}$ alkylene group, the —$(CH_2)_2$— and —$(CH_2)_6$— groups are preferred.

In the formula given above for Y, d may be an integer ranging from 0 to 5, preferably from 0 to 3 and more preferably equal to 1 or 2.

Preferably, B is a linear or branched $C_1$ to $C_{40}$ alkylene group, in particular —$(CH_2)_2$— or —$(CH_2)_6$— or a group:

with $R^5$ being a polyorganosiloxane chain.

As previously discussed, the polyorganosiloxane containing polymer may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

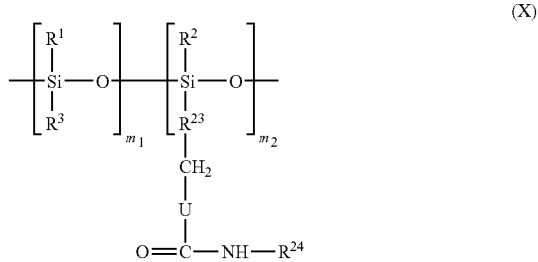

(X)

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used, in the base coat compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups by branching, by reacting these polysiloxanes with monoisocyanates.

As examples of starting polymers of this type containing amino and diamino branches, mention may be made of the polymers corresponding to the following formulae:

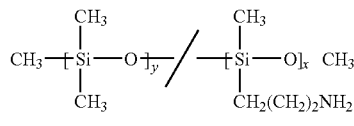

y = 57; x = 3

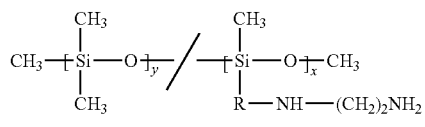

y = 56; x = 4

In these formulae, the symbol "/" indicates that the segments may be of different lengths and in a random order, and R represents a linear aliphatic group preferably containing 1 to 6 carbon atoms, including 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

in which Ph is a phenyl group and n is a number larger than 0, which includes, at least 1, 2 to 500, 2 to 200, from 1 to 300, in particular from 1 to 100, and all values and subranges there between, for example 50.

This polymer is obtained by reacting the following polysiloxane containing amino groups:

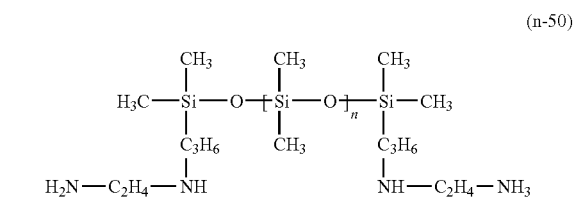

(n-50)

with phenyl isocyanate.

The polymers of formula (VIII) comprising urea or urethane groups in the chain of the silicone polymer may be obtained by reaction between a silicone containing α,ω-$NH_2$ or —OH end groups, of formula:

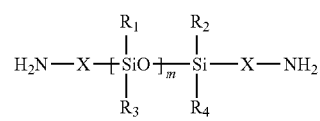

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula $H_2N$—$B^2$—$NH_2$ or HO—$B^2$—OH, in which $B^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone units. In this case, the copolymer may correspond, for example, to the formula:

(XI)

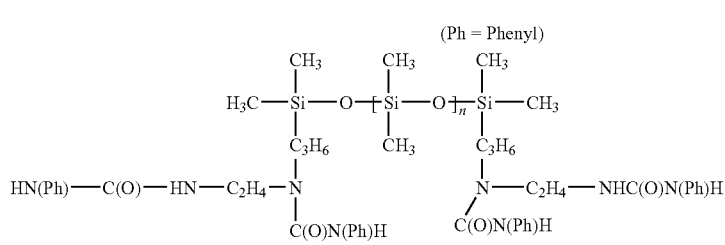

(Ph = Phenyl)

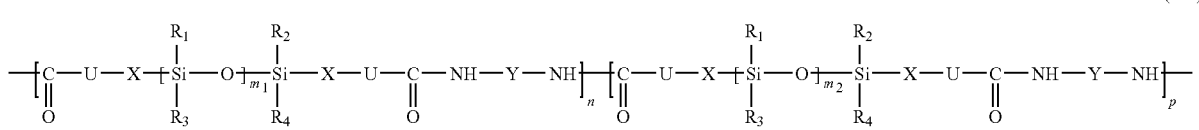

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanate of formula:

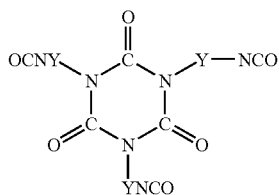

A polyurethane or polyurea silicone containing branches comprising an organosiloxane chain with groups capable of establishing hydrogen interactions is thus obtained. Such a polymer comprises, for example, a moiety corresponding to the formula:

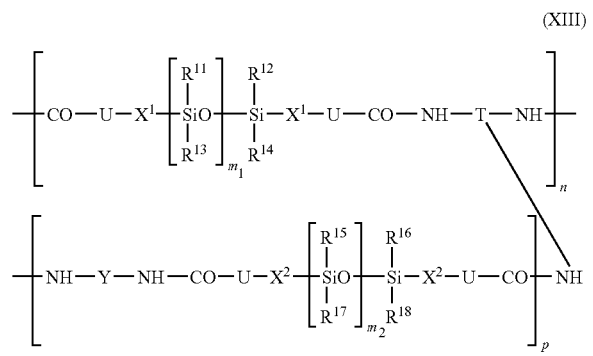

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are as defined above.

As in the case of the polyamides, this copolymer can also comprise polyurethane silicone moieties without branching.

In another embodiment of the invention, the siloxane-based polyureas and polyurethanes that are preferred are:

polymers of formula (VIII) in which m is from 15 to 300, for example, 15 to 100 and all values and subranges there between;

mixtures of two or more polymers in which at least one polymer has a value of m in the range from 15 to 50 and at least one polymer has a value of m in the range from 30 to 300, including all values and subranges there between;

polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;

mixtures of polymer of formula (VIII) combining 1) 80% to 99% by weight of a polymer in which n is equal to 2 to 10 and in particular 3 to 6, and 2) 1% to 20% of a polymer in which n is in the range from 5 to 500 and in particular from 6 to 100, copolymers comprising two moieties of formula (VIII) in which at least one of the groups Y contains at least one hydroxyl substituent;

polymers of formula (VIII) synthesized with at least one portion of an activated diacid (diacid chloride, dianhydride or diester) instead of the diacid;

polymers of formula (VIII) in which X represents —$(CH_2)_3$— or —$(CH_2)_{10}$—; and polymers of formula (VIII) in which the polymers end with a multifunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an α,ω-difunctional block of non-silicone nature, for example a polyester, a polyether or a polyolefin.

Homopolymers or copolymers of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

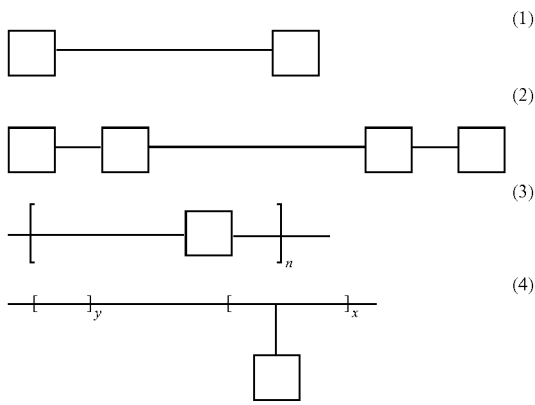

-continued

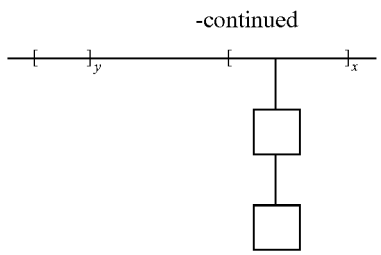

in which the continuous line is the main chain of the siloxane polymer and the squares represent the groups capable of establishing hydrogen interactions.

In case (1), the groups capable of establishing hydrogen interactions are arranged at the ends of the main chain.

In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. In one embodiment, the values n, x and y are such that the polymer has the desired properties in terms of an agent for gelling fatty phases, preferably fatty phases based on non-silicone oil.

As examples of polymers that may be used, mention may be made of the silicone polyamides obtained in accordance with the disclosure in U.S. Pat. No. 5,981,680, the entire disclosure of which is hereby incorporated by reference.

Further examples of polyorganosiloxane containing polymers are set forth in U.S. Pat. Nos. 6,503,632 and 6,569,955, both of which are hereby incorporated by reference in their entirety.

As noted above, the polymers can be solid or liquid at room temperature. When solid, the polymers preferably have a melting point from 40 to 175° C. Most preferably, they have a melting point of from 50 to 130° C., including from 70° C. to 130° C.

As noted above, the polyorganosiloxane containing polymers of the present invention contain both siloxane units and at least two groups capable of establishing hydrogen interactions such as amide linkages. The siloxane units can provide compatibility with a silicone fluid, if present, (for example with the cyclomethicones), while the groups capable of establishing hydrogen interactions and the spacing and selection of the locations of the amide linkages can facilitate gelation and the formation of cosmetic products.

In one embodiment, the polyorganosiloxane containing polymer is present in the base coat composition in an amount effective to provide transfer resistant properties, and may also provide at least one of the following properties: pliability, softness, and wearing comfort. In addition, it is preferred that the base coat compositions of the invention exhibit flexibility and/or good adherence on the keratinous substance to which the compositions have been applied. In another preferred embodiment, the compositions of the present invention when applied to the keratinous substance are substantially non-tacky.

In the base coat composition of the present invention, the polyorganosiloxane-containing polymers are preferably present in an amount of 0.1-80 percent by weight, more preferably from 0.5 to 30 percent by weight and most preferably from 1 to 20 percent by weight of the total weight of the composition.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on a keratinous material. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As is evident, the hardness of the base coat composition according to preferred embodiments of the invention may, for example, be such that the composition is advantageously self-supporting and can disintegrate easily to form a satisfactory deposit on the skin and/or the lips and/or other keratinous materials. In addition, with this hardness, the base coat composition of the invention may have good impact strength.

According to preferred embodiments, the base coat composition in stick form may have the behavior of a deformable, flexible elastic solid, giving noteworthy elastic softness on application. The compositions in stick form of the prior art do not have these properties of elasticity and flexibility.

According to preferred embodiments, cosmetic base coat compositions comprising at least one polyorganosiloxane containing polymer and a liquid fatty phase are provided.

For the purposes of the invention, the expression "liquid fatty phase" means a fatty phase which is liquid at room temperature (25° C.) and atmospheric pressure (760 mmHg, i.e. 101 KPa), composed of one or more fatty substances that are liquid at room temperature, also referred to as oils, that are generally mutually compatible, i.e. forming a homogeneous phase macroscopically. The expression "liquid fatty substance" means a non-aqueous liquid medium which is immiscible in all proportions with water, for example, a hydrocarbon-based compound comprising one or more carbon chains each containing at least 5 carbon atoms and possibly comprising at least one polar group chosen from carboxylic acid, hydroxyl, polyol, amine, amide, phosphoric acid, phosphate, ester, ether, urea, carbamate, thiol, thioether and thioester, a silicone compound optionally comprising carbon chains at the end or pendant, these chains optionally being substituted with a group chosen from fluoro, perfluoro, (poly)amino acid, ether, hydroxyl, amine, acid and ester groups; or a fluoro or perfluoro compound such as fluorohydrocarbons or perfluorohydrocarbons containing at least 5 carbon atoms, possibly comprising a hetero atom chosen from N, O, S and P and optionally at least one function chosen from ether, ester, amine, acid, carbamate, urea, thiol and hydroxyl groups.

The at least one liquid fatty phase, in one embodiment, may comprise at least one oil having an affinity with the polyamide based polymer containing silicone and optionally with the film-forming polymer. The at least one oil, for example, may be chosen from polar oils and apolar oils including hydrocarbon-based liquid oils and oily liquids at room temperature. The polar oils of the invention, for example, may be added to an apolar oil, the apolar oils acting in particular as co-solvent for the polar oils.

The liquid fatty phase of the composition may contain more than 30%, for example, more than 40%, of liquid oil(s) containing a group similar to that of the units of the polyamide based polymer containing silicone, and for example from 50% to 100%. In one embodiment, the liquid fatty phase comprising at least one silicone-polyamide-type skeleton and may contain a high quantity, i.e., greater than 30%, for example greater than 40% relative to the total weight of the liquid fatty phase, or from 50% to 100%, of at least one apolar, such as hydrocarbon-based oil, silicone oils or mixtures thereof. For the purposes of the invention, the expression "hydrocarbon-based oil" means an oil essentially comprising carbon and hydrogen atoms, optionally with at least one group chosen from hydroxyl, ester, carboxyl and ether groups. With such a fatty phase, the at least one film-forming agent may, for example, contain an amine, amide, urethane or silicone group.

For a liquid fatty phase comprising a polymer containing a partially silicone-based skeleton, this fatty phase may contain more than 30%, for example, more than 40%, relative to the total weight of the liquid fatty phase and, for example, from 50% to 100%, of at least one silicone-based liquid oil, relative to the total weight of the liquid fatty phase. In this embodiment, the at least one film-forming agent may comprise a silicone group.

For example, the at least one polar oil useful in the invention may be chosen from:

hydrocarbon-based plant oils with a high content of triglycerides comprising fatty acid esters of glycerol in which the fatty acids may have varied chain lengths from C4 to C24, these chains possibly being chosen from linear and branched, and saturated and unsaturated chains; these oils can be chosen from, for example, wheat germ oil, corn oil, sunflower oil, karite butter, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grape seed oil, blackcurrant seed oil, evening primrose oil, millet oil, barley oil, quinoa oil, olive oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic oils or esters of formula R5COOR6 in which R5 is chosen from linear and branched fatty acid residues containing from 1 to 40 carbon atoms and R6 is chosen from, for example, a hydrocarbon-based chain containing from 1 to 40 carbon atoms, on condition that R5+R6>10, such as, for example, purcellin oil (cetostearyl octanoate), isononyl isononanoate, C12-C15 alkyl benzoates, isopropyl myristate, 2-ethylhexyl palmitate, isostearyl isostearate and alkyl or polyalkyl octanoates, decanoates or ricinoleates; hydroxylated esters such as isostearyl lactate and diisostearyl malate; and pentaerythritol esters;

synthetic ethers containing from 10 to 40 carbon atoms;

C8 to C26 fatty alcohols such as oleyl alcohol; and

C8 to C26 fatty acids such as oleic acid, linolenic acid or linoleic acid.

The at least one apolar oil according to the invention is chosen from, for example, silicone oils chosen from volatile and non-volatile, linear and cyclic polydimethylsiloxanes (PDMSs) that are liquid at room temperature; polydimethylsiloxanes comprising alkyl or alkoxy groups which are pendant and/or at the end of the silicone chain, the groups each containing from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates; hydrocarbons chosen from linear and branched, volatile and non-volatile hydrocarbons of synthetic and mineral origin, such as volatile liquid paraffins (such as isoparaffins and isododecane) or non-volatile liquid paraffins and derivatives thereof, liquid petrolatum, liquid lanolin, polydecenes, hydrogenated polyisobutene such as Parleam®, and squalane; and mixtures thereof. The structured oils, for example those structured with silicone polyamides may be, in one embodiment, apolar oils, such as silicone oils.

In one embodiment, the liquid fatty phase comprises one or more silicone oils, in particular at least one non-volatile oil chosen from phenylsilicones such as phenyl trimethicones.

In another embodiment, the viscosity of the oil according to the invention, in particular silicone oil, is less than 1000 cSt, and for example less than 100 cSt.

In another embodiment, the liquid fatty phase comprises one or more volatile oils chosen from silicone oils. In one embodiment, the volatile silicone oil is chosen from polydimethylsiloxanes, linear or cyclic, having 2 to 7 silicon atoms and optionally having an alkyl group or an alkoxy group having 2 to 10 carbon atoms.

In another embodiment, the liquid fatty phase comprises one or more volatile or nonvolatile hydrocarbon oils and in another embodiment, the liquid fatty phase comprises one or more volatile hydrocarbon oils.

For the purposes of the invention, the expression "volatile solvent or oil" means any non-aqueous medium capable of evaporating on contact with the skin or the lips in less than one hour at room temperature and atmospheric pressure. The volatile solvent(s) of the invention is (are) organic solvents, such as volatile cosmetic oils that are liquid at room temperature, having a non-zero vapor pressure, at room temperature and atmospheric pressure, ranging in particular from 10-2 to 300 mmHg (1.33 to 40 000 Pa) and, for example, greater than 0.03 mmHg (4 Pa) and further example greater than 0.3 mmHg (40 Pa). The expression "non-volatile oil" means an oil which remains on the skin or the lips at room temperature and atmospheric pressure for at least several hours, such as those having a vapor pressure of less than 10-2 mmHg (1.33 Pa).

According to the invention, these volatile solvents may facilitate the staying power or long wearing properties of the composition on the skin, the lips or superficial body growths such as nails and keratinous fibers. The solvents can be chosen from hydrocarbon-based solvents, silicone solvents optionally comprising alkyl or alkoxy groups that are pendant or at the end of a silicone chain, and a mixture of these solvents.

The volatile oil(s), in one embodiment, can be present in an amount ranging from 0% to 95.5% relative to the total weight of the composition, such as from 2% to 75% or, for example, from 10% to 45%. This amount will be adapted by a person skilled in the art according to the desired staying power or long wearing properties.

In practice, the total liquid fatty phase can be, for example, present in an amount ranging from 1% to 99% by weight relative to the total weight of the composition, for example from 5% to 99%, 5% to 95.5%, from 10% to 80% or from 20% to 75%.

The composition of the present invention advantageously also includes one or more film forming agents. Film forming agents are known in the art.

According to preferred embodiments of the present invention, base coat compositions comprise at least one polyorganosiloxane containing polymer and at least one silicone film forming agent.

The Resin MK and Resin MQ silicone resins may form a film after a volatile carrier has evaporated. Depending on the application, plasticizers may be added to help obtain a more flexible, thus more comfortable, film.

Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit $(CH_3)_3SiO_{1/2}$. This unit is considered to be monofunctional because the silicone atom only shares one oxygen when the unit is part of a polymer. The "M" unit can be represented by the following structure:

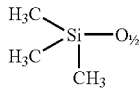

At least one of the methyl groups of the M unit may be replaced by another group, e.g., to give a unit with formula $[R(CH_3)_2]SiO_{1/2}$, as represented in the following structure:

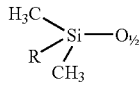

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit $(CH_3)_2SiO_{2/2}$ wherein two oxygen atoms bonded to the silicone atom are used for binding to the rest of the polymer. The "D" unit, which is the major building block of dimethicone oils, can be represented as:

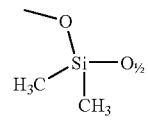

At least one of the methyl groups of the D unit may be replaced by another group, e.g., to give a unit with formula $[R(CH_3)_2]SiO_{1/2}$.

The symbol T denotes the trifunctional unit, $(CH_3)SiO_{3/2}$ and can be represented as:

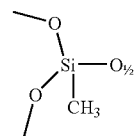

At least one of the methyl groups of the T unit may be replaced by another group, e.g., to give a unit with formula $[R(CH_3)_2]SiO_{1/2}$.

Similarly, the symbol Q denotes the tetrafunctional unit, $SiO_{4/2}$ wherein all four oxygens bonded to the silicone atom are bonded to the rest of the polymer.

Thus, a vast number of different silicone polymers can be manufactured. Further, it would be clear to one skilled in the art that the properties of each of the potential silicone polymers will vary depending on the type(s) of monomer(s), the type(s) of substitution(s), the size of the polymeric chain, the degree of cross linking, and size of any side chain(s).

Non-limiting examples of silicone polymers include silanes, siloxanes, siloxysilicates, and silsesquioxanes. A non-limiting example of such a siloxane is polydimethylsiloxane (PDMS). Polydimethylsiloxanes are generally composed of long straight chains of $(CH_3)_2SiO_{2/2}$ (i.e., D units) and have viscosities which are dependent on both the size of the polymer and the presence and nature of any substituent(s) on the polymer. A non-limiting example of a siloxysilicate is trimethylsiloxysilicate, which may be represented by the following formula:

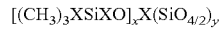

(i.e, MQ units) wherein x and y may, for example, range from 50 to 80. Silsesquioxanes, on the other hand, may be represented by the following formula:

(i.e., T Units) wherein x may, for example, have a value of up to several thousand.

Polymethylsilsesquioxanes are silsesquioxanes that do not have a substituent replacing the methyl groups. Certain polymethylsilsesquioxanes have previously been used in hair care compositions. See, e.g., U.S. Pat. No. 5,246,694, the disclosure of which is incorporated herein by reference, which discloses a shampoo composition comprising a surfactant, an aqueous emulsion of highly viscous silicone in volatile silicone and a cationic polymer which is a derivative of guar gum. The highly viscous silicone disclosed therein may be chosen from silicone resins including a polymethylsilsesquioxane such as Resin MK (also called SiliconHarz MK) which is available from Wacker, and a siloxysilicate such as Resin MQ which is available from General Electric and Dow Corning.

In one embodiment, the silicone film former may be a polymethylsilsesquioxane film former such as Belsil PMS MK, also referred to as Resin MK, available from Wacker Chemie. This polymethylsilsesquioxane film former is a polymer comprising polymerized repeating units of $CH_3SiO_{3/2}$ (T units) and may also contain up to 1% by weight or by mole of units of the formula $(CH_3)_2SiO_{2/2}$ (D units). The weight-average molecular weight of this polymer has been estimated to be 10,000. It is believed that the polymers are in a "cage" and "ladder" configuration, as exemplified in the figures below. The majority of the polymer is in the "ladder" configuration, wherein the ends of the polymer are capped with ethoxy ($CH_3CH_2O$) groups. The ethoxy groups are generally present in an amount of 4.5% by weight and the mole percent is generally 7% (silicone units). As ethoxy groups may react with water, a small and variable amount of SiOH may also be present in the polymer.

methyl T units (88%) and dimethyl D units (12%) and has Si—OH end units), both of which are available from SHIN-ETSU.

Depending on the application, the concentration of the at least one polymethylsilsesquioxane film former in the presently claimed composition may vary considerably. One of skill in the art will be able to determine routinely the amount of the at least one polymethylsilsesquioxane film former depending on the desired application.

In another embodiment, the silicone film former may be chosen from siloxysilicates. Preferably, the siloxysilicate is trimethylsiloxysilicate, which may or may not be in powder form. Trimethylsiloxysilicate (TMS) is commercially available from General Electric under the tradename SR1000 and from Wacker under the tradename TMS 803. TMS is also commercially available from Dow Chemical in a solvent, such as for example, cyclomethicone. However, according to the present invention, TMS may be used in the form of 100% active material, that is, not in a solvent.

Further non-limiting examples of the silicone film formers include silicone/(meth)acrylate copolymers, such as those as described in U.S. Pat. Nos. 5,061,481, 5,219,560, and 5,262,

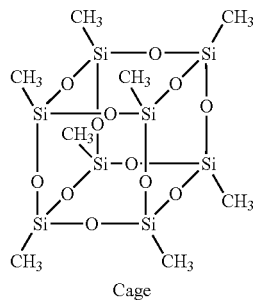

Cage

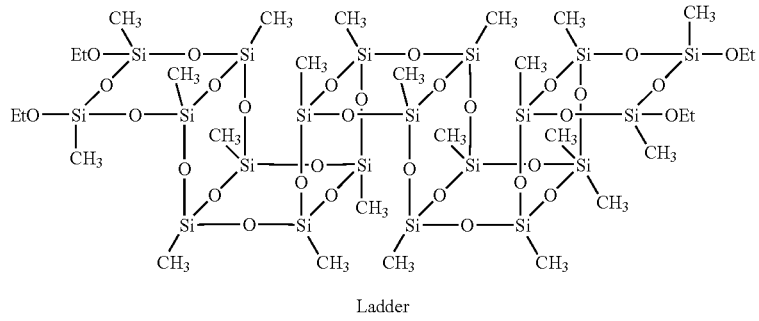

Ladder

Another non-limiting example of the at least one polymethylsilsesquioxane film former suitable for use in the present invention is KR-220L, which is available from SHIN-ETSU. This polymethylsilsesquioxane film former is composed of silicone T-units (i.e., those of formula $CH_3SiO_{3/2}$) and has Si—OH (or silanol) end units. There are no D units in KR-220L.

Another non-limiting example of suitable film formers are alkylphenyl silsesquioxanes such as Wacker SPR-45.

Other non-limiting examples of the at least one polymethylsilsesquioxane film former that may be useful in the practice of the invention include KR-242A (which is comprised of methyl T units (98%) and dimethyl D units (2%) and has Si—OH end units) and KR-251 (which is comprised of 087, the disclosures of which are hereby incorporated by reference. Still further non-limiting examples of silicone film formers are non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545, or acrylates/stearyl acrylate/dimethicone acrylates copolymers, such as those commercially available from Shin-Etsu, for example, the product sold under the tradename KP-561, and acrylates/behenyl acrylate/dimethicone acrylates copolymer, such as those commercially available from Shin-Etsu, for example, the product sold under the tradename KP-562.

Other non-limiting examples of silicone film formers suitable for use in the present invention are silicone esters comprising units of formulae (XIV) and (XV), disclosed in U.S. Pat. Nos. 6,045,782, 5,334,737, and 4,725,658, the disclosures of which are hereby incorporated by reference:

$$R_a R^E_b SiO_{[4-(a+b)/2]} \quad (XIV); \text{ and}$$

$$R'_x R^E_y SiO_{1/2} \quad (XV)$$

wherein

R and R', which may be identical or different, are each chosen from optionally substituted hydrocarbon groups;

a and b, which may be identical or different, are each a number ranging from 0 to 3, with the proviso that the sum of a and b is a number ranging from 1 to 3, x and y, which may be identical or different, are each a number ranging from 0 to 3, with the proviso that the sum of x and y is a number ranging from 1 to 3;

$R^E$, which may be identical or different, are each chosen from groups comprising at least one carboxylic ester.

In one embodiment, $R^E$ groups are chosen from groups comprising at least one ester group formed from the reaction of at least one acid and at least one alcohol. In another embodiment, the at least one acid comprises at least two carbon atoms. In another embodiment, the at least one alcohol comprises at least ten carbon atoms. Non-limiting examples of the at least one acid include branched acids such as isostearic acid, and linear acids such as behenic acid. Non-limiting examples of the at least one alcohol include monohydric alcohols and polyhydric alcohols, such as n-propanol and branched etheralkanols such as (3,3,3-trimethylolpropoxy) propane.

Further non-limiting examples of the at least one silicone film former include liquid siloxy silicates and silicone esters such as those disclosed in U.S. Pat. No. 5,334,737, the disclosure of which is hereby incorporated by reference, such as diisostearoyl trimethylolpropane siloxysilicate and dilauroyl trimethylolpropane siloxy silicate, which are commercially available from General Electric under the tradenames SF 1318 and SF 1312, respectively.

Yet further non-limiting examples of the at least one silicone film former include polymers comprising a backbone chosen from vinyl polymers, methacrylic polymers, and acrylic polymers and at least one chain chosen from pendant siloxane groups and pendant fluorochemical groups. Non-limiting examples of such polymers comprise at least one unit derived from at least one A monomer, at least one unit derived from at least one C monomer, at least one unit derived from D monomers, and, optionally, at least one unit derived from at least one B monomer, wherein:

A, which may be identical or different, are each chosen from free-radically-polymerizable acrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols, and free-radically-polymerizable methacrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols;

B, which may be identical or different, are each chosen from reinforcing monomers which are copolymerizable with at least one A monomer;

C, which may be identical or different, are each chosen from monomers having the formula:

$$X(Y)_n Si(R)_{3-m} Z_m$$

wherein

X is chosen from vinyl groups which are copolymerizable with at least one A monomer and at least one B monomer, Y is chosen from divalent allylene groups, divalent arylene groups, divalent alkarylene groups, and divalent aralkylene groups, wherein the groups comprise from 1 to 30 carbon atoms, and further wherein the groups optionally further comprise at least one group chosen from ester groups, amide groups, urethane groups, and urea groups;

n is zero or 1;

m is a number ranging from 1 to 3;

R, which may be identical or different, are each chosen from hydrogen, $C_1$-$C_4$ alkyl groups, aryl groups, and alkoxy groups; and Z, which may be identical or different, are each chosen from monovalent siloxane polymeric groups; and D, which may be identical or different, are each chosen from free-radically-polymerizable acrylate copolymers and free-radically-polymerizable methacrylate copolymers. Such polymers and their manufacture are disclosed in U.S. Pat. Nos. 5,209,924 and 4,972,037, and WO 01/32737, the disclosures of which are hereby incorporated by reference.

Other non-limiting examples of the at least one silicone film former include silicone/acrylate graft terpolymers, for example, those having the formula:

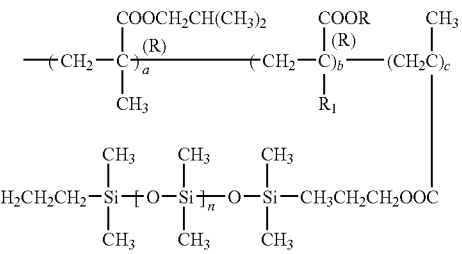

wherein a, b, and c are present in a weight ratio of 69.9:0.1:30 respectively,

R and $R^1$, which may be identical or different, are each chosen from hydrogen and $C_1$-$C_6$ alkyl groups; and m is a number ranging from 100-150.

In an embodiment, m is chosen to provide a macromer having a molecular weight ranging from 8,000 to 12,000, such as 10,000. In another embodiment, m is a number ranging from 124-135, such as 130. Non-limiting examples of these copolymers are described in WO 01/32727 A1, the disclosure of which is hereby incorporated by reference.

Still other examples of suitable silicone film formers include copolymers comprising a backbone chosen from vinyl backbones, methacrylic backbones, and acrylic polymeric backbones and further comprising at least one pendant siloxane group. Non-limiting examples of such polymers are disclosed in U.S. Pat. Nos. 4,693,935, 4,981,903, 4,981,902, the disclosures of which are hereby incorporated by reference.

In an embodiment, the at least one copolymer comprises at least one A monomer, at least one C monomer, and, optionally at least one B monomer, wherein the at least one A monomer is chosen from free-radically-polymerizable vinyl monomers, free-radically-polymerizable methacrylate monomers, and free-radically-polymerizable acrylate monomers; the at least one B monomer, if present, is chosen from at least one reinforcing monomer copolymerizable with the at least one A monomer, and the at least one C monomer is chosen from monomers having the formula:

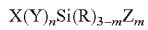

wherein:

X is chosen from vinyl groups which are copolymerizable with the at least one A monomer and with the at least one B monomer;

Y is chosen from divalent groups;

n is zero or 1;

m is a number ranging from 1 to 3;

R, which may be identical or different, are each chosen from hydrogen, optionally substituted $C_1$-$C_{10}$ alkyl groups, optionally substituted phenyl groups, and optionally substituted $C_1$-$C_{10}$ alkoxy groups; and Z, which may be identical or different, are each chosen from monovalent siloxane polymeric groups.

Non-limiting examples of A monomers include methacrylic acid esters of $C_1$-$C_{12}$ linear alcohols, methacrylic acid esters of $C_1$-$C_{12}$ of branched alcohols, styrene monomers, vinyl esters, vinyl chloride monomers, vinylidene chloride monomers, and acryloyl monomers.

Non-limiting examples of B monomers include acrylic monomers comprising at least one group chosen from hydroxyl, amino, and ionic groups, and methacrylic monomers comprising at least one group chosen from hydroxyl, amino, and ionic groups. Non-limiting examples of ionic groups include quaternary ammonium groups, carboxylate salts, and sulfonic acid salts.

The C monomers are the same as those described for the C monomers in the previous paragraphs.

Other non-limiting examples of the silicone film-former include a copolymer chosen from vinyl-silicone graft copolymers having the following formula and vinyl-silicone block copolymers having the following formula:

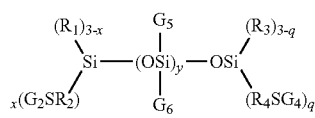

wherein $G_5$, which may be identical or different, are each chosen from alkyl groups, aryl groups, aralkyl groups, alkoxy groups, alkylamino groups, fluoroalkyl groups, hydrogen, and -ZSA groups, wherein A is chosen from vinyl polymeric segments comprising at least one polymerized free-radically-polymerizable monomer, and Z is chosen from divalent $C_1$-$C_{10}$ alkylene groups, divalent aralkylene groups, divalent arylene groups, and divalent alkoxylalkylene groups. In an embodiment Z is chosen from methylene groups and propylene groups.

$G_6$, which may be identical or different, are each chosen from alkyl groups, aryl groups, aralkyl groups, alkoxy groups, alkylamino groups, fluoroalkyl groups, hydrogen, and -ZSA groups, as defined above;

$G_2$ comprises A;

$G_4$ comprises A;

$R_1$, which may be identical or different, are each chosen from alkyl groups, aryl groups, aralkyl groups, alkoxy groups, alkylamino groups, fluoroalkyl groups, hydrogen, and hydroxyl. In one embodiment, $R_1$ is chosen from $C_1$-$C_4$ alkyl groups, such as methyl groups, and hydroxyl.

$R_2$, which may be identical or different, are each chosen from divalent $C_{1-10}$ alkylene groups, divalent arylene groups, divalent aralkylene groups, and divalent alkoxyalkylene groups. In one embodiment, $R_2$ is chosen from divalent $C_1$-$C_3$ alkylene groups and divalent $C_7$-$C_{10}$ aralkylene groups. In another embodiment, $R_2$ is chosen from —$CH_2$— groups and divalent 1,3-propylene groups.

$R_3$, which may be identical or different, are each chosen from alkyl groups, aryl groups, aralkyl groups alkoxy groups, alkylamino groups, fluoroalkyl groups, hydrogen, and hydroxyl. In one embodiment, $R_3$ is chosen from $C_1$-$C_4$ alkyl groups and hydroxyl. In another embodiment, $R_3$ is chosen from methyl groups.

$R^4$, which may be identical or different, are each chosen from divalent $C_1$-$C_{10}$ alkylene groups, divalent arylene groups, divalent aralkylene groups, and divalent alkoxyalkylene groups. In one embodiment, $R^4$ is chosen from divalent $C_1$-$C_3$ alkylene groups and divalent $C_7$-$C_{10}$ aralkylene groups. In another embodiment, $R^4$ is chosen from divalent —$CH_2$— groups and divalent 1,3-propylene groups.

x is a number ranging from 0 to 3;

y is a number greater than or equal to 5. In an embodiment, y ranges from 10 to 270, and in another embodiment, y ranges from 40 to 270.

q is a number ranging from 0 to 3;

Non-limiting examples of these polymers are described in U.S. Pat. No. 5,468,477, the disclosure of which is hereby incorporated by reference. A non-limiting example of such polymers is poly(dimethylsiloxane)-g-poly(isobutyl methacrylate), which is commercially available from 3M Company under the tradename VS 70 IBM.

According to preferred embodiments, the silicone film former is present in the composition in an amount ranging from 0.1% to 30% by weight relative to the total weight of the composition. Preferably, the silicone film former is present in an amount ranging from 0.5% to 20% by weight relative to the total weight of the composition, and more preferably from 1% to 10%. One of ordinary skill in the art will recognize that the silicone film former of the present invention may be commercially available, and may come from suppliers in the form of a dilute solution. The amounts of the silicone film former disclosed herein therefore reflect the weight percent of active material.

In a preferred embodiment, the polyorganosiloxane polymer and the film forming agent are solid. The composition is prepared by heating the solids to a temperature sufficient to combine and form compositions as described herein. This combination of solid polyorganosiloxane polymer and film forming agent provide beneficial transfer-resistant, long-wear compositions.

According to preferred embodiments, base coat compositions comprising at least one polyorganosiloxane containing polymer and at least one coloring agent are provided. Preferably, such colored cosmetic compositions are lip compositions (for example, lipstick or liquid lip colors).

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%.

The base coat compositions comprising at least one polyorganosiloxane containing polymer are anhydrous or may comprise water. By "anhydrous," it is meant that the composition contains substantially no water (that is, less than about 0.1% by weight of the composition of water). If present, water is preferably present in an amount ranging from about 0.1 to about 70%, preferably from about 0.5 to 50%, and more preferably from about 1 to about 30% relative to the total weight of the composition.

Additional Additives

The compositions described herein can also, independently, comprise any additive usually used in the field under consideration. For example, dispersants such as poly(12-hydroxystearic acid), antioxidants, essential oils, preserving agents, fragrances, waxes, liposoluble polymers that are dispersible in the medium, fillers, neutralizing agents, cosmetic and dermatological active agents such as, for example, emollients, moisturizers, vitamins, essential fatty acids, sunscreens, and mixtures thereof can be added. Further examples of suitable additional components can be found in the references which have been incorporated by reference in this application. Still further examples of such additional ingredients may be found in the *International Cosmetic Ingredient Dictionary and Handbook* (9$^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

The compositions described herein advantageously contain at least one cosmetic active agent and/or at least one dermatological active agent, i.e., an agent having a beneficial effect on the skin, lips or body growths and/or at least one coloring agent.

Emollients and/or humectants that may be used in the compositions of the invention include glycerin, propylene glycol, and emollients and other similar ingredients disclosed in the *International Cosmetic Ingredient Dictionary and Handbook Vol.* 4 (9$^{th}$ ed. 2002), more particularly the emollients disclosed on pages 2930-2936. The disclosure of the *International Cosmetic Ingredient Dictionary and Handbook Vol.* 4, pages 2930-2936, is hereby incorporated by reference.

Plasticizers may also be added to the compositions to improve the flexibility and cosmetic properties of the resulting formulation. Plasticizers are materials which soften synthetic polymers. They are frequently required to avoid brittleness and cracking of film formers. One skilled in the art may routinely vary the amount of plasticizer desired based on the properties desired and the application envisaged. Plasticizers useful in the practice of the invention include lecithin, polysorbates, dimethicone copolyol, glycols, citrate esters, glycerin, dimethicone, and other similar ingredients disclosed in the *International Cosmetic Ingredient Dictionary and Handbook Vol.* 4 (9$^{th}$ ed. 2002), more particularly the plasticizers disclosed on page 2927. The disclosure of the *International Cosmetic Ingredient Dictionary and Handbook Vol.* 4, page 2927, is hereby incorporated by reference.

The compositions may also contain sunscreens. In certain embodiments, the combination of the polysiloxane-containing polymer when combined with one or more sunscreens improves, quite significantly, the overall SPF value of the composition relative to a composition without the polysiloxane-containing polymer. These are variously described in U.S. Pat. Nos. 2,463,264, 4,367,390, 5,166,355 and 5,237,071 and in EP-0,863,145, EP-0,517,104, EP-0,570,838, EP-0,796,851, EP-0,775,698, EP-0,878,469, EP-0,933,376, EP-0,893,119, EP-0,669,323, GB-2,303,549, DE-1,972,184 and WO-93/04665, also expressly incorporated by reference. A wide variety of sunscreens is described in U.S. Pat. No. 5,087,445, issued to Haffey et al. on Feb. 11, 1992; U.S. Pat. No. 5,073,372, issued to Turner et al. on Dec. 17, 1991; and Chapter VIII of *Cosmetics and Science and Technology* by Segarin et al., pages 189 et seq. (1957), all of which are incorporated herein by reference in their entirety.

According to the present invention, the compositions described herein may further comprise at least one filler. As used herein, the term "filler" means any particle that is solid at room temperature and atmospheric pressure, used alone or in combination, which does not react chemically with the various ingredients of the emulsion and which is insoluble in these ingredients, even when these ingredients are raised to a temperature above room temperature and in particular to their softening point or their melting point. In an embodiment, the at least one filler has a melting point at least greater than 1700° C., for example, greater than 2000° C. In an embodiment, the at least one filler may have an apparent diameter ranging from 0.01 μm to 150 μm, such as from 0.5 μm to 120 μm, for example from 1 μm to 80 μm. An apparent diameter corresponds to the diameter of the circle into which the elementary particle fits along its shortest dimension (thickness for leaflets). Further, the at least one filler may be absorbent, i.e., capable in particular of absorbing the oils of the composition and also the biological substances secreted by the skin, may be surface-treated, e.g., to make it lipophilic, and/or may be porous so as to absorb the sweat and/or sebum secreted by the skin.

The at least one filler may be chosen from inorganic and organic fillers, and may have any shape such as lamellar, spherical and/or oblong. Non-limiting examples of the at least one inert filler include talc, mica, silica, kaolin, polyamide powders (such as Nylon® powder, and such as the product sold by Atochem as Orgasol®), poly-β-alanine powders, polyethylene powders, acrylic polymer powders (such as polymethyl methacrylate (PMMA) powder, for instance the product sold by Wacker as Covabead LH-85 (particle size 10-12 μm) and the acrylic acid copolymer powder sold by Dow Corning as Polytrap®), polytetrafluoroethylene (Teflon®) powders, lauroyllysine, boron nitride, silica, kaolin, starch, starch derivatives, hollow polymer microspheres (such as those hollow polymer microspheres formed from polyvinylidene chloride and acrylonitrile, for instance the product sold by Nobel Industrie as Expancel®), and polymerized silicone microspheres (such as those polymerized silicone microspheres sold by Toshiba as Tospearl®), precipitated calcium carbonate, magnesium carbonate and hydrocarbonate, hydroxyapatite, ceramic microcapsules, polyester particles and coated elastomers such as products sold under the denomination KSP (KSP110, KSP 200, KSP 300) sold by Shin Etsu and/or those described in U.S. Pat. No. 5,538,793, the disclosure of which is hereby incorporated by reference.

These additives may be present in the compositions in a proportion from 0% to 20% (such as from 0.01% to 20%) relative to the total weight of the composition and further such as from 0.01% to 10% (if present).

The compositions described herein can be in the form of a tinted or non tinted dermatological composition or a care composition for keratin materials such as the skin, the lips and/or other keratinous materials. It can be used in particular as a care base for the skin or the lips (e.g., lip balms, for protecting the lips against cold and/or sunlight and/or the wind). As defined herein, a deodorant product is personal hygiene product and does not relate to care, make-up or treatment of keratin materials, including keratinous fibers.

The compositions of the invention may also be in the form of a colored make-up product for the skin, optionally having care or treating properties, a blusher, a face powder, an eye shadow, a concealer product, an eyeliner, a make-up product for the body; a make-up product for the lips such as a lipstick, optionally having care or treating properties; a make-up product for superficial body growths such as the nails or the eyelashes, in particular in the form of a mascara cake, or for the eyebrows and the hair, in particular in the form of a pencil.

Needless to say, the compositions described herein should be cosmetically or dermatologically acceptable, i.e., it should contain a non-toxic physiologically acceptable medium and should be able to be applied to the skin, superficial body growths or the lips of human beings. For the purposes of the invention, the expression "cosmetically acceptable" means a composition of pleasant appearance, odor, feel and/or taste.

According to preferred embodiments of the present invention, methods of treating, caring for and/or making up keratinous material such as skin, lips, and other keratinous materials by applying compositions of the present invention to the keratinous material in an amount sufficient to treat, care for and/or make up the keratinous material are provided. In a particularly preferred mode of applying the compositions of the present invention, the base coat is applied first and then the top coat is applied on to the base coat.

According to other preferred embodiments, methods of covering or hiding defects associated with keratinous material such as imperfections or discolorations by applying compositions of the present invention to the keratinous material in an amount sufficient to cover or hide such defects are provided. In a preferred mode of applying layered compositions of the present invention, a base coat is applied first and then a top coat is applied over the base coat.

According to yet other preferred embodiments, methods of enhancing the appearance of keratinous material by applying compositions of the present invention to the keratinous material in an amount sufficient to enhance the appearance of the keratinous material are provided. In a preferred mode of applying bilayer compositions of the present invention, the base coat is applied first and then the top coat is applied over the base coat.

In accordance with the preceding preferred embodiments, the compositions of the present invention are applied topically to the desired area of the skin in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects. The composition is preferably applied to the desired area that is dry or has been dried prior to application. In a preferred mode of applying bilayer compositions of the present invention, a base coat is applied first and then a top coat is applied on to the base coat. If necessary, the base coat is allowed to dry prior to the application of the top coat. The top coat may cover all of the surface covered by the base coat or only a part of the surface and preferably a majority of the surface covered by the base coat.

According to a preferred embodiment of the present invention, compositions having improved cosmetic properties such as, for example, improved long wear, transfer resistance or waterproof properties are provided. The improved properties may also be chosen from improved flexibility, wearability, drying time or retention as well as reduced tackiness or migration over time.

The present invention also provides kits and/or prepackaged materials suitable for consumer use containing at least one composition or combination of compositions according to the description herein. The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds. The kit and/or prepackaged material may contain combinations of the compositions described herein as well as instructions or suggestions for use of the composition or compositions contained within the kit and/or prepackaged material.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1

A top coat preparation can be prepared as follows:

| Phase | INCI Name | Trade Name | % by weight |
|---|---|---|---|
| A | TRIMETHYL PENTAPHENYL TRISILOXANE | DC 555 COSMETIC FLUID | 74.80 |
|  | bis-diglyceryl polyacyladipate-2 | Softisan 649 | 15.00 |
|  | tocopheryl acetate | DL alpha tocopheryl acetate | 0.20 |

-continued

| Phase | INCI Name | Trade Name | % by weight |
|---|---|---|---|
| B | MICROCRYSTALLINE WAX | MICROCRYSTALLINE WAX SP 624 | 3.00 |
|  | Ozokerite | Ozokerite SP1020 | 4.00 |
|  | beeswax | beeswax | 3.00 |
|  | total = |  | 100.00 |

Combine Phase A ingredients together into a beaker, then transfer the beaker to a 100° C. oil bath and mix with a propeller mixer until uniform.

Add Phase B ingredients into Phase A and mix with a propeller mixer until the waxes completely melt and uniform.

Pour the bulk into a mold at 90-95° C., then chill the mold at a freezer for about 30 min.

Take out the products and fill into the components.

Example 2

A base coat preparation can be prepared as follows:

| Phase | INCI Name | Trade Name | % by weight |
|---|---|---|---|
| A | ISODODECANE | PERMETHYL 99A | 37.57 |
|  | trimethylsyloxysilicate | SR 1000 | 17.00 |
|  | NYLON-611/DIMETHICONE COPOLYMER | DC 2-8179 GELLANT- | 11.33 |
|  | DISTEARDIMONIUM HECTORITE/isododecane/propylene carbonate 10/87/3 | Bentone gel ISD V | 25.00 |
| B | Iron Oxides | red Iron Oxide | 2.05 |
|  | yellow 6 | FDC yellow 6 Al Lake | 0.79 |
|  | Red 7 Lake | DC Red 7 W | 0.42 |
|  | blue 1 | blue 1 lake | 0.14 |
|  | titanium dioxide | titanium dioxide | 1.98 |
| C | titanium dioxide & mica | Timiron super gold | 2.50 |
|  | MICA | MICA CONCORD 1000 | 1.12 |
|  | FRAGRANCE |  | 0.10 |
|  | total = |  | 100.00 |

Combine Phase A ingredients together into a beaker, then transfer the beaker to a 90° C. oil bath and mix with a propeller mixer until the DC gellant completely melt and the system uniform.

Combine Phase B ingredients together into Phase A and then transfer the mixture to a Disconti Ball Mill and mill the mixture for about 40 minutes.

Transfer the mixture into a beaker and then add Phase C ingredients and mix with a propeller mixer at room temperature until it uniform.

Add a fragrance into the mixture and mix with a propeller mixer for about 5 min.

Transfer the resulting fluid to individual packages.

After applying the top coat over the base coat on the lips, the resultant make-up will appear glossy and shiny.

Example 3

A lipstick formulation can be prepared as follows:

| Phase | INCI Name | Trade Name | % by weight |
|---|---|---|---|
| A | Trimethyl pentaphenyl Trisiloxane | DC 555 Cosmetic Fluid | 63.25 |
|  | Bis-glyceryl polyacryladipate-2 | Softisan 649 | 5.00 |
|  | Sucrose acetate isobutyrate | SAIB Food Grade | 15.37 |
|  | Total oils |  | 83.62 |
| B | Iron Oxides | Red Iron Oxide | 2.05 |
|  | Yellow 6 | FDC yellow 6 Al Lake | 0.79 |
|  | Red 7 | DC Red 7 | 0.42 |
|  | Blue 1 | Blue lake 1 | 0.14 |
|  | Titanium dioxide | Titanium dioxide | 1.98 |
|  | Total color pigments |  | 5.38 |
| C | Mica | Mica concord 1000 | 4.00 |
| D | Polyethylene wax | PE400 | 3.00 |
|  | Polyethylene wax | PE 500 | 4.00 |
|  | total = |  | 100.00 |

Combine Phase A ingredients together into a beaker, then transfer the beaker to a 90° C. oil bath and mix with a propeller mixer until the system uniform.

Combine Phase B ingredients together into Phase A and then transfer the mixture to a Disconti Ball Mill and mill the mixture for about 40 minutes.

Transfer the mixture of phase B into a beaker and then add Phase C ingredients and mix with a propeller mixer at 100° C. until it is uniformed.

Add waxes of Phase D into the mixture and mix with a propeller mixer until it is uniformed at 100° C.

Reduce the temperature to 85-90° C. for 5 to 10 minutes.

Pour the bulk into a mold at 90-95° C., then chill the mold at a freezer for about 30 min.

Take out the products and fill into the components.

Example 4

A top coat formulation can be prepared as follows:

| Phase | INCI Name | Trade Name | % by weight |
|---|---|---|---|
| A | Trimethyl pentaphenyl Trisiloxane | DC 555 Cosmetic Fluid | 69.10 |
|  | Sucrose acetate isobutyrate | SAIB Food Grade | 20.00 |
|  | Benzophenone-3 | Uvinul M 40 | 3.00 |
|  | Ethylhexyl methoxycinnamate | Parasol MCX | 7.50 |
|  | Isopropylparaben, isobutylparaben | Liquapar oil | 0.40 |

Combine Phase A ingredients together into a beaker, then mix with a propeller mixer until the system uniform at 90° C.

Take out the products and fill into the components.

Example 5

A SOLID LIPSTICK formulation can be prepared as follows:

| PHASE | INCI Name | Trade Name | % by weight |
|---|---|---|---|
| A | TRIMETHYL PENTAPHENYL TRISILOXANE | DC 555 COSMETIC FLUID | 18.34 |
|   | bis-diglyceryl polyacyladipate-2 | Softisan 649 | 12.00 |
|   | SUCROSE ACETATE ISOBUTYRATE | SAIB FOOD GRADE | 30.00 |
|   | POLY PHENYL TRIMETHICONE | Wacker-Belsil PDM 1000 | 2.00 |
|   | PHENYL TRIMETHICONE | DC556 | 12.00 |
|   | Total oils |  | 74.34 |
| B | SUCROSE ACETATE ISOBUTYRATE | SAIB FOOD GRADE | 2.60 |
|   | C12-15 alkyl benzoate | Finsolv | 1.33 |
|   | TRIMETHYL PENTAPHENYL TRISILOXANE | DC 555 COSMETIC FLUID | 2.67 |
|   | Iron Oxides | Brown Iron Oxide | 1.185 |
|   | yellow 6 | FDC yellow 6 Al Lake | 0.125 |
|   | Iron Oxides | Black Iron Oxide | 0.465 |
|   | Red 7 Lake | DC Red 7 W | 0.425 |
|   | titanium dioxide | titanium dioxide | 1.630 |
|   | total phase B |  | 10.43 |
| C | MICA | MICA | 2.00 |
|   | pearl | GT TAN OPAL | 2.744 |
|   | pearl | Timiron Super Blue | 1.856 |
|   | pearl | Timiron Super Slv Fn | 1.63 |
|   | total phase C |  | 8.23 |
| D | Polyethylene | Performalene 400 | 3.00 |
|   | Polyethylene | Performalene 500 | 4.00 |
|   | total phase D |  | 7.00 |
|   | total = |  | 100.00 |

Combine Phase A ingredients together into a beaker, then transfer the beaker to a 90° C. oil bath and mix with a propeller mixer until the system uniform.

Combine Phase B ingredients together and then transfer the mixture to a three rolling Mill and mill the mixture for 5 rolling times.

Transfer the mixture of phase B into a beaker and then add Phase C ingredients and mix with a propeller mixer at 100° C. until it is uniformed.

Add waxes of Phase D into the mixture and mix with a propeller mixer until it is uniformed a 100° C.

Reduce the temperature to 85-90° C. for 5 to 10 minutes.

Pour the bulk into a mold at 90-95° C., then chill the mold at a freezer for about 30 min.

Take out the products and fill into the components.

Example 6

Liquid Lip Gloss

| PHASE | INCI Name | Trade Name | % by weight |
|---|---|---|---|
| A | TRIMETHYL PENTAPHENYL TRISILOXANE | DC 555 COSMETIC FLUID | 20.00 |
|   | bis-diglyceryl polyacyladipate-2 | Softisan 649 | 8.00 |
|   | SUCROSE ACETATE ISOBUTYRATE | SAIB FOOD GRADE | 58.00 |
|   | POLY PHENYL TRIMETHICONE | Wacker-Belsil PDM 1000 | 5.25 |
|   | propylene carbonate | propylene carbonate | 0.90 |
|   | disteardimonium hectorium | bentone hectorite | 3.00 |
|   | Total oils |  | 95.15 |
| B | SUCROSE ACETATE ISOBUTYRATE | SAIB FOOD GRADE | 0.78 |
|   | C12-15 alkyl benzoate | Finsolv | 0.40 |
|   | TRIMETHYL PENTAPHENYL TRISILOXANE | DC 555 COSMETIC FLUID | 0.80 |
|   | Iron Oxides | Brown Iron Oxide | 0.356 |
|   | yellow 6 | FDC yellow 6 Al Lake | 0.038 |
|   | Iron Oxides | Black Iron Oxide | 0.140 |
|   | Red 7 Lake | DC Red 7 W | 0.128 |
|   | titanium dioxide | titanium dioxide | 0.489 |
|   | total phase B |  | 3.13 |
| C | MICA | Mica concord 1000 | 0.72 |
|   | pearl | GT TAN OPAL | 0.43904 |
|   | pearl | Timiron Super Blue | 0.29696 |
|   | pearl | Timiron Super Slv Fn | 0.2608 |
|   | total phase C |  | 1.72 |
|   | total = |  | 100.00 |

Combine Phase A ingredients together into a beaker, then transfer the beaker to a 90° C. oil bath and mix with a propeller mixer until the system uniform.

Combine Phase B ingredients together and then transfer the mixture to a three rolling Mill and mill the mixture for 5 rolling times.

Transfer the mixture of phase B into a beaker and then add Phase C ingredients and mix with a propeller mixer at room temperature until it is uniformed.

Take out the products and fill into the components.

The invention claimed is:

1. A composition suitable for topical administration to a keratinous surface, which comprises at least one phenyl substituted organosiloxane and sucrose acetate isobutyrate in an amount of 40% to 60% by weight of the composition, wherein the at least one phenyl substituted organosiloxane is defined by

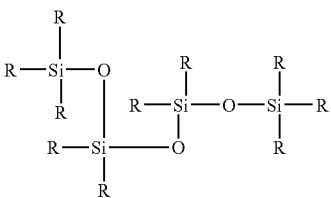

wherein R is a methyl or phenyl and wherein there are at least three phenyl groups in the organosiloxane; or

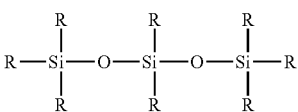

wherein R is a methyl or phenyl and wherein the organosiloxane comprises at least three phenyl groups wherein the at least one phenyl substituted organosiloxane is present in an amount from 10 to 95% by weight of the composition and the composition further comprises at least one wax.

2. The composition of claim 1, wherein the at least one phenyl substituted organosiloxane is defined by the following formula:

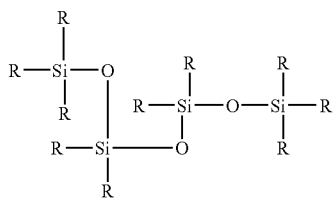

wherein R is a methyl or phenyl and wherein there are at least three phenyl groups in the organosiloxane.

3. The composition of claim 2, wherein the organosiloxane comprises at least four phenyl groups.

4. The composition of claim 2, wherein the organosiloxane comprises five phenyl groups.

5. The composition of claim 1, wherein the phenyl substituted organosiloxane is defined by the following formula:

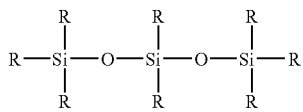

wherein R is a methyl or phenyl and wherein the organosiloxane comprises at least three phenyl groups.

6. The cosmetic composition of claim 5, wherein the organosiloxane comprises at least four phenyl groups.

7. The cosmetic composition of claim 5, wherein the organosiloxane comprises five phenyl groups.

8. The cosmetic composition of claim 1, which comprises a mixture of two or more phenyl substituted organosiloxanes.

9. The cosmetic composition of claim 8, wherein the mixture comprises two or more of triphenyl substituted organosiloxane, tetraphenyl substituted organosiloxane, and pentyl phenyl substituted organosiloxane.

10. A kit or prepackaged material comprising at least one composition according to claim 1.

11. A method of making-up, caring for, treating, and/or covering or hiding defects in a keratinous surface in need thereof, comprising applying to the keratinous surface at least one composition according to claim 1.

12. The cosmetic composition of claim 1, wherein the at least one phenyl substituted organosiloxane is present in an amount from 20 to 80% by weight of the composition.

13. The cosmetic composition of claim 1, wherein the at least one wax is ozokerite.

14. The cosmetic composition of claim 1, wherein the at least one wax is beeswax.

15. The cosmetic composition of claim 1, wherein the composition is essentially free of volatile compounds.

16. The cosmetic composition of claim 1, wherein the composition is devoid of volatile compounds.

17. The cosmetic composition of claim 1, wherein the composition is anhydrous.

* * * * *